United States Patent
Park et al.

(10) Patent No.: US 9,514,274 B2
(45) Date of Patent: Dec. 6, 2016

(54) LAYERED MEDICAL IMAGE FORMING, RECEIVING, AND TRANSMITTING METHODS

(71) Applicant: Infinitt Healthcare Co., Ltd., Seoul (KR)

(72) Inventors: Un Sok Park, Gwangmyeong-si (KR); Hwa Seok Park, Seoul (KR); Hyun Chul Jung, Incheon (KR)

(*) Notice: Subject to any disclaimer, the term of this patent is extended or adjusted under 35 U.S.C. 154(b) by 36 days.

(21) Appl. No.: 14/603,372

(22) Filed: Jan. 23, 2015

(65) Prior Publication Data

US 2016/0154932 A1    Jun. 2, 2016

(30) Foreign Application Priority Data

Nov. 29, 2014 (KR) .................. 10-2014-0169244
Jan. 21, 2015 (KR) .................. 10-2015-0010212

(51) Int. Cl.
  G06K 9/00     (2006.01)
  G06F 19/00    (2011.01)
  G06T 7/00     (2006.01)
  G06T 11/60    (2006.01)

(52) U.S. Cl.
  CPC ........... G06F 19/321 (2013.01); G06T 7/0012 (2013.01); G06T 11/60 (2013.01)

(58) Field of Classification Search
  USPC .......................................... 382/128
  See application file for complete search history.

(56) References Cited

U.S. PATENT DOCUMENTS

| | | | | |
|---|---|---|---|---|
| 6,584,216 B1* | 6/2003 | Nyul | .............. | G06T 5/009 250/474.1 |
| 2008/0140722 A1* | 6/2008 | Jakobovits | ............ | G06F 19/321 |
| 2011/0216950 A1* | 9/2011 | Illmann | .............. | G06F 19/321 382/128 |
| 2011/0320469 A1* | 12/2011 | Canessa | .............. | G06F 17/3028 707/758 |
| 2012/0128221 A1* | 5/2012 | Lazebnik | ............. | A61B 8/463 382/131 |
| 2012/0229490 A1* | 9/2012 | Rezaee | ................. | G09G 5/10 345/589 |
| 2013/0195329 A1* | 8/2013 | Canda | .................. | G06F 19/321 382/128 |
| 2014/0015856 A1* | 1/2014 | Xiao | .................... | A61B 5/0033 345/629 |
| 2014/0143298 A1* | 5/2014 | Klotzer | .............. | H04L 67/2823 709/203 |
| 2014/0143299 A1* | 5/2014 | Klotzer | ................ | G06F 19/321 709/203 |
| 2015/0149565 A1* | 5/2015 | Ahmed | ................ | H04L 65/403 709/206 |
| 2015/0150092 A1* | 5/2015 | Raizada | ................ | H04L 63/10 726/4 |
| 2015/0278442 A1* | 10/2015 | Rezaee | ................ | G06F 19/321 382/128 |

* cited by examiner

*Primary Examiner* — John Strege
(74) *Attorney, Agent, or Firm* — Antonio Ha & U.S. Patent, LLC

(57) ABSTRACT

A layered medical image forming method includes a layered medical image forming step of layering first to n-th value of interest look-up table (VOI LUT)-applied medical images (where n is a natural number), which are obtained by applying first to n-th VOI LUTs included in variation information of the original of a medical image to the original of the medical image so as to allow another system to display the same variation information.

13 Claims, 2 Drawing Sheets

LAYERED MEDICAL IMAGE FORMING, RECEIVING, AND TRANSMITTING METHODS

CROSS-REFERENCE TO RELATED APPLICATION

This application claims priority to and the benefit of Korean Patent Application No. 10-2014-0169244 filed on Nov. 29, 2014, and Korean Patent Application No. 10-2015-0010212 filed on Jan. 21, 2015, the disclosures of which are incorporated by reference herein in their entireties.

BACKGROUND

1. Technical Field

The present invention relates to methods of forming, receiving, and transmitting layered medical images, and more particularly, to methods of forming, receiving, and transmitting layered medical images in which GSPS information can be read together with examination information and metadata can be transmitted upon a first request for examination information in order to complete processing according to a single request in a web browser, JPEG images can be received and processed together in the form of a layered image (original+GSPS+VOI+LUT1+VOI LUT2) in order to transmit the PEG images to which a VOI LUT has been applied, and thus time that is spent calling a web server several times in the related art can be reduced.

2. Discussion of Related Art

A DICOM study, which is a collection of medical images in the related art, has a structure of study-series-image. That is, one study includes a plurality of series and one series includes a plurality of images. In this structure, information of modality series corresponding to gray scale softcopy presentation state (GSPS) (PR) information has to be separately requested and it takes time to acquire the information of modality series in a Web environment. Here, GSPS (PR) is a DICOM standard for allowing another system to display the same variation information (such as rotation, zoom, and pan and scroll).

When applying a value of interest look-up table (VOI LUT) for an image, as client terminal has to separately acquire the VOI LUT and newly render the image. At this time, a web browser first display's a JPEG image and has to transmit and receive the VOI LUT to and from a server because the client terminal cannot render the VOI LUT.

SUMMARY

The present invention is directed to methods of forming, receiving, and transmitting methods layered medical images in which GSPS information can be read together with examination information and metadata can be transmitted upon a first request for the examination information in order to complete processing according to a single request in a web browser, JPEG images can be received and processed together in the form of a layered image (original+GSPS+VOI LUT1+VOI LUT2) so as to transmit the JPEG images to which a VOI LUT has been applied, and thus time that is spent calling a web server several times in the related art can be reduced.

According to an aspect of the present invention, there is provided a layered medical image forming method including a layered medical image forming step of layering first to n-th value of interest look-up table (VOI LUT)-applied medical images (where n is a natural number), which are obtained by applying first to nth VOI LUTs included in variation information of the original of a medical image to the original of the medical image so as to allow another system to display the same variation information.

The variation information may include only VOI LUT information or the variation information may include the VOI LUT information and one or more of rotation information, zoom information, pan and scroll information, annotation information, and shutter information.

The variation information may be included in a header of the original of the medical image when the variation information includes only the VOI LUT information, and the variation information may be included in a gray scale softcopy presentation state (GSPS) file, which is a DICOM standard, when the variation information includes the VOI LUT information and one or more of rotation information, zoom information, pan and scroll information, annotation information, and shutter information.

The layered medical image forming step may include a step of including a GSPS in a header of the original of the medical image.

According to another aspect of the invention, there is provided a layered medical image receiving method including: a medical image requesting step of causing a client terminal to request a medical image; a layered medical image forming step of layering first to nth value of interest look-up table (VOI LUT)-applied medical images (where n is a natural number), which are obtained by applying first to nth VOI LUTs included in variation information at the original of the medical image to the original of the medical image so as to allow another system to display the same variation information; and a layered medical image displaying step of displaying the layered medical image on the client terminal.

The variation information may include only VOI LUT information, or the variation information may include the VOI LUT information and one or more of rotation information, zoom information, pan and scroll information, annotation information, and shutter information.

The variation information may be included in a header of the original of the medical image when the variation information includes only the VOI LUT information, and the variation information may be included in a gray scale softcopy presentation state (GSPS) file, which is as DICOM standard, when the variation information includes the VOI LUT information and one or more of rotation information, zoom information, pan and scroll information, annotation information, and shutter information.

The layered medical image forming step may include a step of including a GSPS in a header of the original of the medical image.

The layered medical image receiving method may further include a VOI LUT-applied medical image displaying step of displaying the VOI LUT-applied medical image of a layer in the layered medical image on the client terminal when a VOI LUT corresponding to the variation information of the original of the medical image selected by the client terminal is present.

According to still another aspect of the invention, there is provided as layered medical image transmitting method including: a medical image requesting step of causing a client terminal to request a medical image; a layered medical image forming step of layering first to nth value of interest look-up table (VOI LUT)-applied medical images (where n is a natural number), which are obtained by applying first to n-th VOI LUTs included in variation information of the original of the medical image to the original of the medical image so as to allow another system to display the same variation information; and a layered medical image providing step of providing the layered medical image to the client terminal.

The variation information may include only VOI LUT information, or the variation information may include the VOI LUT information and one or more of rotation information, zoom information, pan and scroll-information, annotation information, and shutter information.

The variation information may be included in a header of the original of the medical image when the variation information includes only the VOI LUT information, and the variation information may be included in a gray scale softcopy presentation state (GSPS) file, which is a DICOM standard, when the variation information includes the VOI LUT information and one or more of rotation information, zoom information, pan and scroll information, annotation information, and shutter information.

The layered medical image forming step may include a step of including a GSPS in a header of the original of the medical image.

The layered medical image transmitting method may further include a VOI LUT-applied medical image displaying step of displaying the VOI LUT-applied medical image of as layer in the layered medical image on the client terminal when a VOI LUT corresponding to the variation information of the original of the medical image selected by the client terminal is present.

In the methods of forming, receiving, and transmitting layered medical images according to the present invention, first, it is possible to read GSPS information together with examination information and transmit metadata upon a first request for the examination information in order to complete processing according to a single request in a web browser.

Second, it is possible to receive and process PEG images together in the form of a layered image (original+GSPS+VOI LUT1+VOI LUT2) so as to transmit the JPEG images to which a VOI LUT has been applied.

Third, it is possible to reduce time that is spent calling a web server several times.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
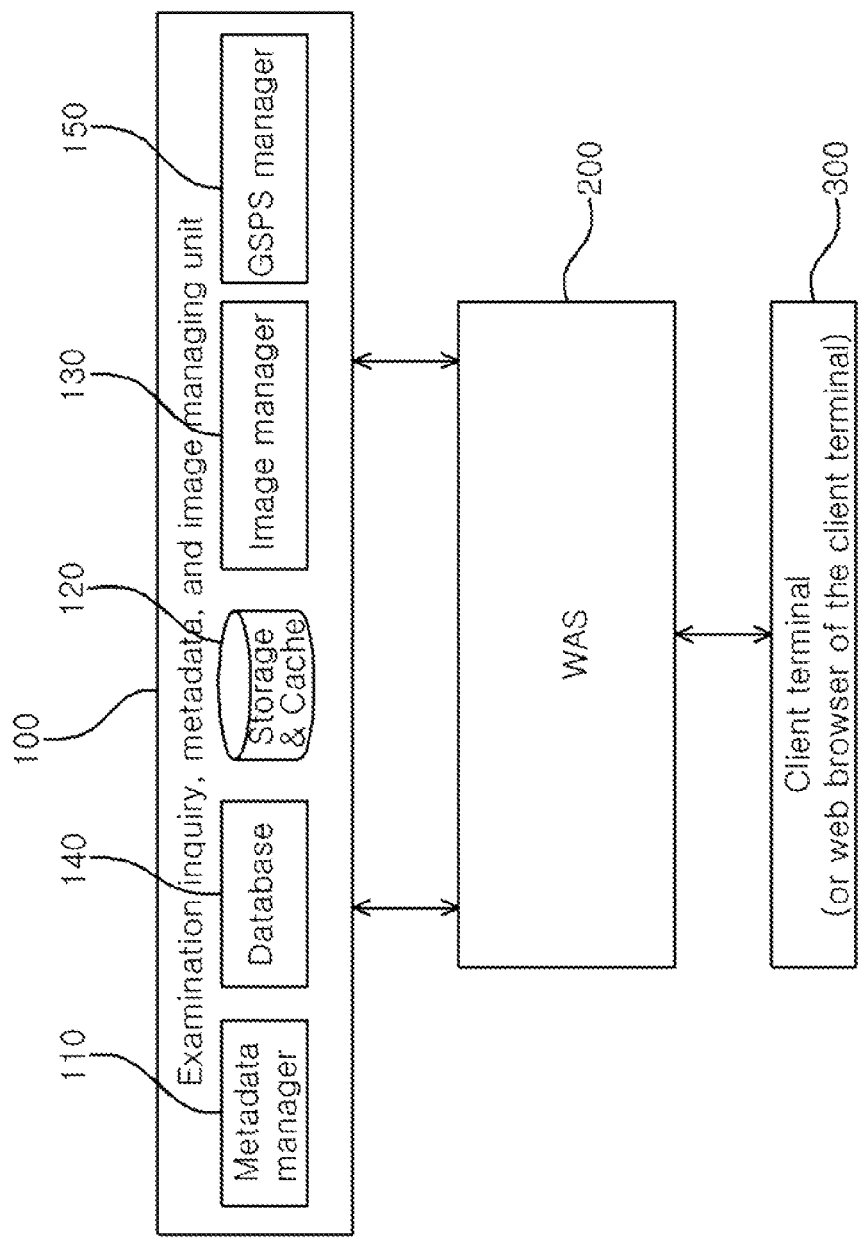
FIG. 1 is a block diagram illustrating a configuration of a system to which methods of forming, receiving, and transmitting layered medical images according to exemplary embodiments of the present invention are applied.

Exemplary embodiments of the present invention will be described in detail below with reference to the accompanying drawings. Terms or words used in this description or the appended claims should not be analyzed to have general or colloquial meanings, but should be analyzed to have meanings and concepts corresponding to the technical spirit of the present invention, on the basis of the principle that an inventor can appropriately define concepts of terms for the purpose of explaining the present invention in a best mode.

Therefore, embodiments described in this description and the configurations illustrated in the drawings are merely best exemplary embodiments of the present invention and do not represent all the technical spirit of the present invention. Accordingly, it should be understood by those skilled in the in that there may be various equivalents and modifications with which the exemplary embodiments can be replaced at the time of filing of the present invention.

Figure 2:
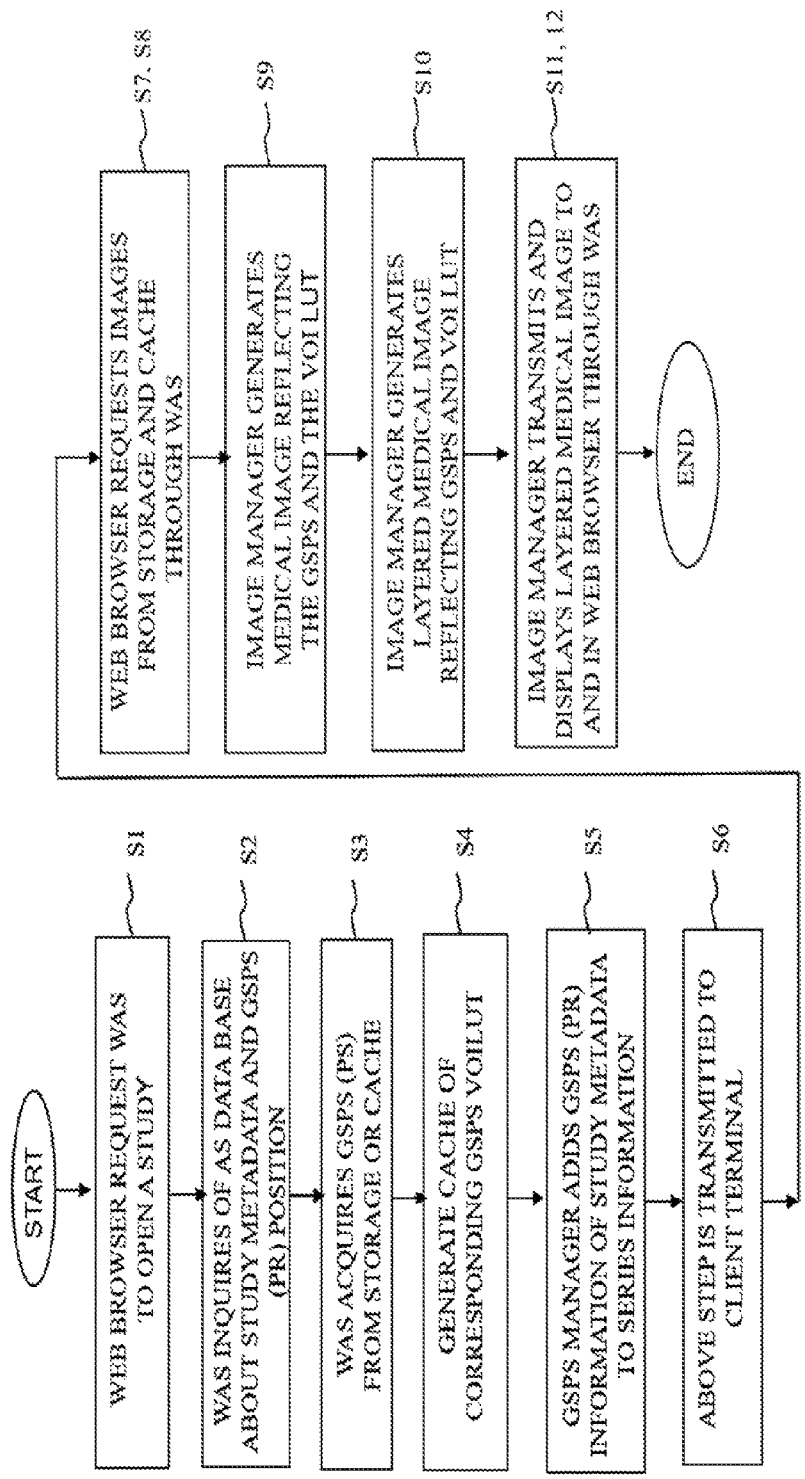
FIG. 2 is a flowchart illustrating an example of the methods of forming, receiving, and transmitting layered medical images according to the exemplary embodiments of the present invention.

FIG. 1 is a block diagram illustrating a configuration of a system to which methods of forming, receiving, and transmitting layered medical images according to exemplary embodiments of the present invention are applied. FIG. 2 is a flowchart illustrating an example of the methods of forming, receiving, and transmitting layered medical images according to the exemplary embodiments of the present invention.

Referring to FIGS. 1 and 2, a layered medical image forming method according to the present invention includes as layered medical image forming step of layering first to n-th value of interest look-up table (VOI LUT)-applied medical images (where n is a natural number), which are obtained by applying first to n-th VOI LUTs included in variation information of the original of a medical image to the original of the medical image so as to allow another system to display the same variation information.

Here, the "variation information" may include only VOI LUT information. In this case, the "variation information" is included in the header of the original of he medical image.

Alternatively, the "variation information" may include the VOI LUT information and one or more of rotation information, zoon information, pan and scroll information, annotation information, and shutter information. In this case, the "variation information" is included in a gray scale softcopy presentation state (GSPS) file, which is a DICOM standard.

The layered medical image forming step may include a step of including a GSPS in the header of the original of the medical image.

Specifically, referring to FIG. 1, the system to which the present invention is applied includes an examination inquiry, metadata, and image managing unit 100 that manages metadata and images and performs a storage and cache function, a web application server (WAS) 200 that manages and transmits data, and a client terminal (or a web browser of the client terminal) 300.

As illustrated in FIG. 2, the web browser 300 requests the WAS 200 to open a study (first step, S1). The WAS 200 inquires of as database 140 about study metadata and a GSPS (PR) position (second step, S2). The WAS 200 acquires the GSPS (PR) from a storage and cache 120 (third step, S3). Then, the WAS 200 reconstructs GSPS information, which is in units of images, in units of series and generates a cache of the corresponding GSPS VOI LUT (fourth step, S4). A GSPS manager 150 adds the GSPS (PR) information of the study metadata to the series information (fifth step, 55). The data generated in the fifth step is a data structure of examination (study). In order to open a study, the client terminal 300 requires the data structure of the study (that is, study-series-images). Accordingly, the study data structure generated in the fifth step may be transmitted to the client terminal 300 (sixth step, S6) and images may be requested using the transmitted data structure in a seventh step. That is, the web browser 300 requests the images from the storage and cache 120 through the WAS 200 (seventh step and eighth step, S7 and S8). An image manager 130 generates a medical image reflecting the GSPS and the VOI LUT (ninth step, S9). The image manager 130 generates a layered medical image reflecting the GSPS and the VOI LUT (tenth step, S10). The image manager 130 transmits and displays the layered medical image to and in the web browser 300 through the WAS 200 (eleventh step and twelfth step, S11 and S12).

In the related art, in order to view a desired medical image, the VOI LUT of the medical image has to be applied thereto. When applying the VOI LUT of the medical image, the client terminal 300 has to separately receive the VOI LUT from the server and newly render the VOI LUT. At this time, the web browser of the client terminal first displays a JPEG image. Since the client terminal cannot render the LUT, the client terminal has to transmit the LUT to the server and receive the rendered LUT from the server. However, according to the present invention, the processing speed is very high, and thus the layer of a desired medical image only has to be selected from a layered medical image.

The present invention also provides a layered medical image receiving method including: a medical image requesting step of causing a client terminal to request medical image; a layered medical image forming step of layering first to n-th value of interest look-up table (VOI LUT)-applied medical images (where n is a natural number), which are obtained by applying first to n-th VOI LUTs included in variation information of the original of the medical image to the original of the medical image so as to allow another system to display the same variation information; and a layered medical image displaying step of displaying the layered medical image on the client terminal. The layered medical image receiving method may further include a VOI LUT-applied medical image displaying step of displaying the VOI LUT-applied medical image of a layer in the layered medical image on the client terminal when a VOI LUT corresponding to the variation information of the original of the medical image selected by the client terminal is present.

In addition, the present invention provides a layered medical image transmitting method including: a medical image requesting step of causing a client terminal to request a medical image; a layered medical image forming step of layering first to n-th value of interest look-up table (VOI LUT)-applied medical images (where n is a natural number), which are obtained by applying first to n-th VOI LUTs included in variation information of the original of the medical image to the original of the medical image so as to allow another system display the same variation information; and a layered medical image providing step of providing the layered medical image to the client terminal.

What is claimed is:

1. A layered medical image forming method by an image managing unit performing a storage and cache function, the method comprising:
   a layered medical image forming step of layering first to n-th value of interest look-up table (VOI LUT)-applied medical images (where n is a natural number), which are obtained by applying first to n-th VOI LUTs included in variation information of the original of a medical image to the original of the medical image so as to allow another system to display the same variation information,
   wherein the variation information is included in a header of the original of the medical image when the variation information includes VOI LUT information but does not include one or more of rotation information, zoom information, pan and scroll information, annotation information, and shutter information, and the variation information is included in a gray scale softcopy presentation state (GSPS) file when the variation information includes the VOI LUT information along with one or more of the rotation information, the zoom information, the pan and scroll information, the annotation information, and the shutter information.

2. The layered medical image forming method according to claim 1, wherein the variation information includes only the VOI LUT information, or wherein the variation information includes the VOI LUT information and one or more of rotation information, zoom information, pan and scroll information, annotation information, and shutter information.

3. The layered medical image forming method according to claim 1, wherein the layered medical image forming step includes a step of including a GSPS in a header of the original of the medical image.

4. A layered medical image receiving method by an image managing unit performing a storage and cache function, the method comprising: a medical image requesting step of causing a client terminal to request a medical image; a layered medical image forming step of layering first to nth value of interest lookup table (VOI LUT)-applied medical images (where n is a natural number), which are obtained by applying first to nth VOI LUTs included, in variation information of the original of the medical image to the original of the medical image so as to allow another system to display the same variation information; and a layered medical image displaying step of displaying the layered medical image on the client terminal,
   wherein the variation information is included in a header of the original of the medical image when the variation information includes VOI LUT information but does not include one or more of rotation information, zoom information, pan and scroll information, annotation information, and shutter information, and the variation information is included in a gray scale softcopy presentation state (GSPS) file when the variation information includes the VOI LUT information along with one or more of the rotation information, the zoom information, the pan and scroll information, the annotation information, and the shutter information.

5. The layered medical image receiving method according to claim 4, wherein the variation information includes only the VOI LUT information, of wherein the variation information includes the VOI LUT information and one or more of rotation information, zoom information pan and scroll information, annotation information, and shutter information.

6. The layered medical image receiving method according to claim 4, wherein the layered medical image forming step includes a step of including a GSPS in a header of the original of the medical image.

7. The layered medical image receiving method according to claim 4, further comprising a VOI LUT-applied medical image displaying step of displaying the VOI LUT-applied medical image of a layer in the layered medical image on the client terminal when a VOI LUT corresponding to the variation information of the original of the medical image selected by the client terminal is present.

8. A layered medical image transmitting method by an image managing unit performing a storage and cache function, the method comprising: a medical image requesting step of causing a client terminal to request a medical image; a layered medical image forming step of layering first to n-th value of interest look-up table (VOI LUT)-applied images (where n is a natural number), which are obtained by applying first to n-th VOI LUTs included in variation information of the original of the medical image to the original of the medical image so as to allow another system to display the same variation information, and a layered medical image providing step of providing the layered medical image to the client terminal, wherein the variation information is included in a header of the original of the medical image when the variation information includes VOI LUT information but does not include one or more of rotation information, zoom information, pan and scroll information, annotation information, and shutter information, and the variation information is included in a gray scale softcopy presentation state (GSPS) file when the variation information includes the VOI LUT information along with one or more of the rotation information, the zoom information, the pan and scroll information, the annotation information, and the shutter information.

9. The layered medical image transmitting method according to claim 8, wherein the variation information includes only the VOI LUT information, or where the variation information includes the VOI LUT information and one or more of rotation information, pan and scroll information, annotation information, and shutter information.

10. The layered medical image transmitting method according to claim 8, wherein the layered medical image forming step includes a step of including a GSPS in a header of the original of the medical image.

11. The layered medical image transmitting method according to claim 8, further comprising a VOI LUT-applied medical image displaying step of displaying the VOI LUT-applied medical image of a layer in the layered medical image on the client terminal when a VOI LUT corresponding to the variation information of the original of the medical image selected h the client terminal is present.

12. The layered medical image forming method according to claim 1, further comprising reading the GSPS information together with examination information and transmitting metadata upon a first request for the examination information in order to complete processing according to a single request in a web browser.

13. The layered medical image forming method according to claim 1, wherein the medical image includes a joint photographic experts group (JPEG) image, and wherein the JPEG image is transmitted, received, or processed in a form of a layered image including the original, the GSPS file, and the first to the n-th VOI LUTs.

* * * * *